United States Patent
Kumagai et al.

(10) Patent No.: US 11,838,994 B2
(45) Date of Patent: Dec. 5, 2023

(54) DETERMINATION DEVICE AND HEATING COOKING APPARATUS

(71) Applicant: SHARP KABUSHIKI KAISHA, Sakai (JP)

(72) Inventors: Munesato Kumagai, Sakai (JP); Masahiro Ikehara, Sakai (JP)

(73) Assignee: SHARP KABUSHIKI KAISHA, Sakai (JP)

(*) Notice: Subject to any disclaimer, the term of this patent is extended or adjusted under 35 U.S.C. 154(b) by 331 days.

(21) Appl. No.: 17/185,230

(22) Filed: Feb. 25, 2021

(65) Prior Publication Data

US 2021/0289587 A1  Sep. 16, 2021

(30) Foreign Application Priority Data

Mar. 11, 2020  (JP) ................ 2020-042033

(51) Int. Cl.
  *A47J 37/08*  (2006.01)
  *H05B 1/02*  (2006.01)
  *G01N 21/55*  (2014.01)
  *A47J 36/32*  (2006.01)
  *G01N 33/10*  (2006.01)

(52) U.S. Cl.
  CPC ............ *H05B 1/0261* (2013.01); *A47J 36/32* (2013.01); *A47J 37/085* (2013.01); *G01N 21/55* (2013.01); *G01N 33/10* (2013.01)

(58) Field of Classification Search
  CPC ....... H05B 1/0261; A47J 36/32; A47J 36/321; A47J 37/06; A47J 37/08; A47J 37/0807; A47J 37/085; A47J 37/0857; A47J 37/0871; G01N 33/10; G01N 21/25; G01N 21/251; G01N 21/255; G01N 21/27; G01N 21/55; G01N 21/64; G01N 21/88; G01N 21/8851; G01N 21/89; G01N 21/9501; G01N 21/95607
  See application file for complete search history.

(56) References Cited

U.S. PATENT DOCUMENTS

| | | | | |
|---|---|---|---|---|
| 4,433,232 A | * | 2/1984 | Tachikawa | F24C 7/08 219/709 |
| 2003/0010776 A1 | | 1/2003 | Kang et al. | |
| 2016/0278576 A1 | * | 9/2016 | Manning | A47J 37/0871 |

FOREIGN PATENT DOCUMENTS

| | | | | |
|---|---|---|---|---|
| JP | H01314825 A | 12/1989 | | |
| JP | H05-264042 A | 10/1993 | | |
| JP | H08266424 A | 10/1996 | | |
| JP | 2003-42455 A | 2/2003 | | |
| WO | WO-2016121628 A1 | * | 8/2016 | ............. G01N 21/64 |

* cited by examiner

*Primary Examiner* — Hung D Nguyen
(74) *Attorney, Agent, or Firm* — ScienBiziP, P.C.

(57) ABSTRACT

A toaster according to the disclosure includes a light receiving unit configured to receive reflected light from bread being cooked and a surface condition determination unit configured to determine a surface condition of the bread being cooked on the basis of intensity of the reflected light received by the light receiving unit.

9 Claims, 5 Drawing Sheets

DETERMINATION DEVICE AND HEATING COOKING APPARATUS

CROSS-REFERENCE TO RELATED APPLICATIONS

This application claims the benefit of priority to Japanese Patent Application Number 2020-042033 filed on Mar. 11, 2020. The entire contents of the above-identified application are hereby incorporated by reference.

BACKGROUND

Technical Field

The disclosure relates to a determination device that determines a condition of a foodstuff being cooked and a heating cooking apparatus provided with the determination device.

In heat cooking apparatuses such as toasters or ovens for common households (e.g., a heating cooking apparatus disclosed in JP H5-264042 A (published on Oct. 12, 1993)), set temperatures, cooking times, and the like recommended by the manufacturer are set as cooking menus for target foodstuffs that are frequently cooked. Then, the user uses or refers to the cooking menus to perform the desired heating process. These cooking menu settings may be set by the user individually in terms of temperature and time as described above, or may be performed by selecting a menu name or the like, such as "bread" or "roasted chicken", that is appropriately provided as a set of settings in which individual settings are put together in advance. In any case, these set values are derived under certain standard conditions set by the manufacturer regarding the amount, size, and the like of foodstuffs, and the heating process is performed while performing monitoring with a temperature sensor or the like in a cooking chamber so that heating cooking proceeds in accordance with this design. Nowadays, for example, to suit the user's preference, some devices may have such a certain adjustment range with respect to the standard settings that the "doneness of bread" can be set to several levels such as "dark" or "light".

SUMMARY

However, in the existing heating cooking apparatuses described above, when the conditions of the foodstuff to be cooked such as the size, moisture, and temperature, or the ambient temperature, the usage history of the device, and the like are largely different from the above-mentioned standard conditions, the intended result cannot be obtained. For example, failures such as "insufficient heating" and "burning" of foodstuffs often occur. To deal with such problems, some devices adjust the heating temperature and time on the basis of other parameters such as "temperature change in the cooking chamber" and "humidity" to ensure that the intended and designed result is obtained as much as possible, but it is difficult to obtain a sufficient result. Especially, the difference of appearance, such as "doneness of the foodstuff at the surface thereof", is difficult to be visually judged, and the difference may change significantly in a short time. Thus, the deviation from the standard conditions cannot be adjusted, and the result may differ largely from the desired result. In a case that the result is "insufficient heating", the user can try to reach the intended result by performing additional heating process as appropriate, but it will take time and effort accordingly. In an opposite case, that is, in a case of "excess heating", the foodstuff is burned and has to be given up. That is, with existing heating cooking apparatuses, the surface condition (browned condition) of the foodstuff being cooked cannot be appropriately determined, so that there arises the problem that it is difficult to obtain the desired doneness of the foodstuff.

An object of one aspect of the disclosure is to achieve a determination device and a heating cooking apparatus capable of appropriately determining a surface condition of a foodstuff being cooked.

To solve the above problems, a determination device according to one aspect of the disclosure includes a light receiving unit configured to receive reflected light from a foodstuff being cooked and a surface condition determination unit configured to determine a surface condition of the foodstuff being cooked on the basis of intensity of the reflected light received by the light receiving unit.

According to one aspect of the disclosure, the surface condition of the foodstuff being cooked can be appropriately determined.

BRIEF DESCRIPTION OF DRAWINGS

The disclosure will be described with reference to the accompanying drawings, wherein like numbers reference like elements.

DESCRIPTION OF EMBODIMENTS

First Embodiment

An embodiment of the disclosure will be described in detail below. In the embodiment, an example in which the determination device of the disclosure is applied to a toaster, which is an example of a heating cooking apparatus, and an object to be heated is bread will be described.

Toaster

Figure 1:
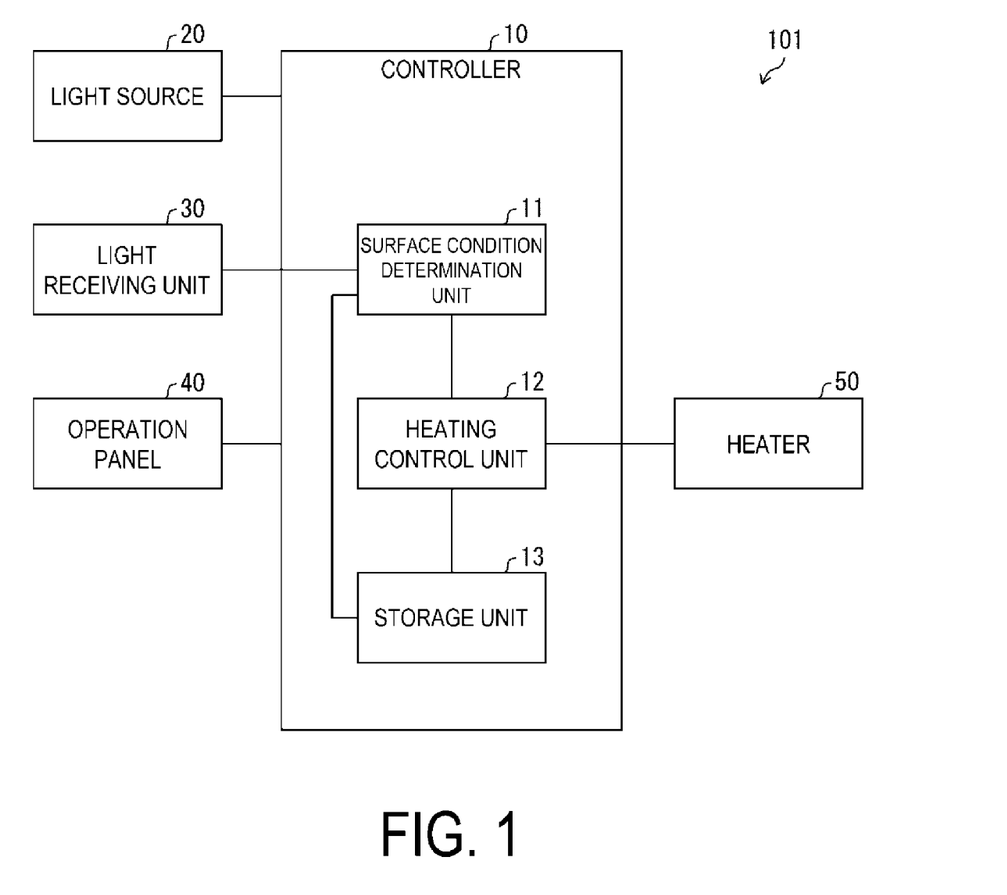
FIG. 1 is a schematic block diagram of a heating cooking apparatus according to a first embodiment of the disclosure.
Figure 2:
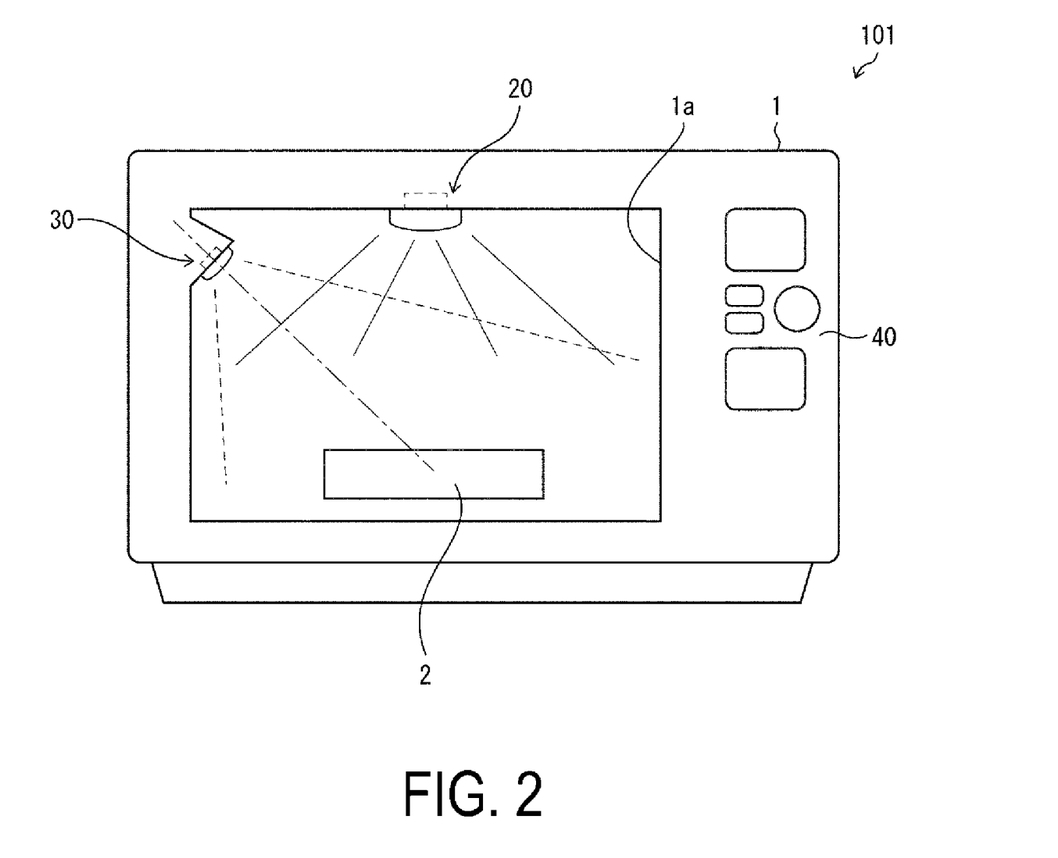
FIG. 2 is a schematic configuration diagram of the heating cooking apparatus illustrated in FIG. 1.

FIG. 1 is a schematic block diagram of a toaster 101. FIG. 2 is a schematic configuration diagram of the toaster 101.

In the toaster 101, as illustrated in FIG. 2, a bread (object to be heated) 2 is placed in a heating chamber 1a of a rectangular parallelepiped casing 1 and cooked by heating.

In the heating chamber 1a, in addition to a heater 50 (FIG. 1) that heats the bread 2, a light source 20 and a light receiving unit 30 that are used to determine the browned condition of the bread 2 (surface condition of the object to be heated) are provided.

The light source 20 is disposed on the top surface of the heating chamber 1a because the bread 2 placed in the heating chamber 1a is irradiated with light. Accordingly, the arrangement position of the light source 20 is not limited to the top surface of the heating chamber 1a, and may be disposed at any position as long as the bread 2 placed in the heating chamber 1a can be irradiated with light. Further, the wavelength of the light emitted by the light source 20 is not limited to a specific wavelength. Accordingly, an internal light (not illustrated) already provided in the heating chamber 1a may be used in place of the light source 20.

The light receiving unit 30 is disposed on a side surface of the heating chamber 1a and receives the reflected light from the bread 2 placed in the heating chamber 1a. That is, the light emitted from the light source 20 hits the bread 2, and the light receiving unit 30 receives the light reflected from the surface of the bread 2. Accordingly, the arrangement position of the light receiving unit 30 is not limited to the side surface of the heating chamber 1a, and may be disposed at any position as long as the light receiving unit 30 can receive the reflected light from the bread 2 placed in the heating chamber 1a. Note that the details of the light receiving unit 30 will be described later.

The casing 1 is provided with an operation panel 40 for a user to operate the toaster 101. The operation panel 40 receives the user's operation and transmits an instruction to a controller 10 illustrated in FIG. 1.

Controller 10

The controller 10 includes a surface condition determination unit 11, a heating control unit 12, and a storage unit 13.

The surface condition determination unit 11 determines the browned (color) condition of the bread 2 (surface condition of the bread 2) from the reflected light of the bread 2 received by the light receiving unit 30. That is, the browned condition of the bread 2 being cooked (heated) is determined. Note that the details of the determination of the browned condition of the bread 2 by the surface condition determination unit 11 will be described later.

The heating control unit 12 controls the heating using the heater 50 on the basis of the determination result from the surface condition determination unit 11. Note that the details of the heating control using the heater 50 by the heating control unit 12 will be described later.

The storage unit 13 stores numerical values (wavelength of reflected light and intensity ratio of light) shown in the graph of FIG. 3 which will be described later, the determination result of the surface condition determination unit 11, information necessary for determining the browned condition of the bread 2 being cooked, and information indicating the processing content of the heating control and the like using the heater 50 by the heating control unit 12.

Determination of Browned Condition of Bread 2

Figure 3:
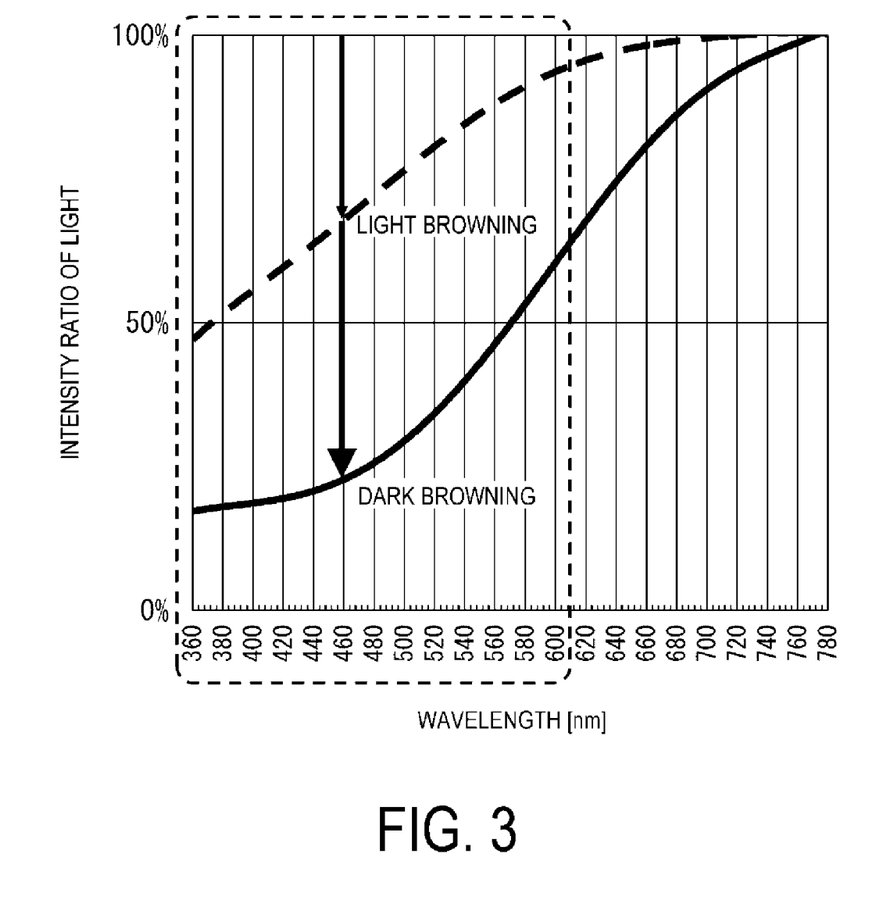
FIG. 3 is a graph showing the progress of browning and the change in light.

FIG. 3 is a graph showing the relationship between the wavelength of the reflected light from the bread 2 and the intensity ratio of the reflected light. The graph shows that in the reflected light reflected from the surface of the bread 2, the light having a wavelength in the range of 600 nm or less is attenuated with a good response to the progress of the browning. Thus, from the graph, the browned (color) condition (surface condition) of the bread 2 can be determined. Note that the lower limit of the wavelength range of the reflected light is not particularly limited, but it is realistic and preferable that the wavelength be 360 nm, which is the lowest visible wavelength to the human eye.

Specifically, the reflected light is detected in the wavelength range of 600 nm or less, and the browned condition of the bread 2 is determined from the intensity ratio of the detected reflected light. The intensity ratio of the reflected light here is calculated using the intensity of the reflected light from the bread 2 before heating process as an initial value, then using the initial value as a denominator, and using the intensity of the reflected light from the bread 2 after the heating process as a numerator. In this case, the intensity of the reflected light from the bread 2 decreases when the heating process progresses and the browned color becomes darker. Therefore, as shown in FIG. 3, the intensity ratio of the reflected light decreases from 100% in accordance with the progress of the browning. For example, in a case where the wavelength of the detected reflected light is 600 nm, when the intensity ratio of the reflected light is close to 100%, the surface condition of the bread 2 is determined to be "light browning", and on the contrary, when the intensity ratio of reflected light becomes lower with respect to 100%, the surface condition of the bread 2 is determined to be "dark browning". That is, when the intensity ratio of light is 100%, it indicates that the bread 2 is not browned, and when the intensity ratio of light is less than 100%, it indicates that the bread 2 is browned. Therefore, the smaller the intensity ratio of light is with respect to 100%, the darker the browning color of the bread 2.

Note that, in the above example, the intensity of the reflected light from the bread 2 before the heating process is used as the initial value and the initial value is used as the denominator of the intensity ratio. However, no such limitation is intended. Even when the intensity of the reflected light during the heating process is used as the initial value for the subsequent heating process and used as the denominator of the intensity ratio, the browned condition of the bread 2 can be determined. In addition, instead of the intensity ratio based on such an initial value, the absolute value of the intensity of the reflected light from the bread 2 may be used to determine the browned condition of the bread 2. A calculation parameter suitable for the intended situation may be used for determining the browned condition of the bread 2.

The browned condition (surface condition) of the bread 2 is determined by the surface condition determination unit 11 described above. That is, values indicating the wavelength of the light reflected from the bread 2 received by the light receiving unit 30 and the intensity ratio of the light are transmitted to the surface condition determination unit 11. Then, the surface condition determination unit 11 determines the surface condition of the bread 2 being cooked, that is, the browned condition, from the numerical values stored in the storage unit 13 (wavelength of reflected light and intensity ratio of light).

To determine the browned condition of the bread 2 as accurately as possible, it is necessary to detect an accurate light intensity ratio. That is, the light receiving unit 30 needs to receive the reflected light in a way that the intensity ratio of light can be detected as accurately as possible. The details of the light receiving unit 30 will be described below.

Light Receiving Unit 30

Figure 4:
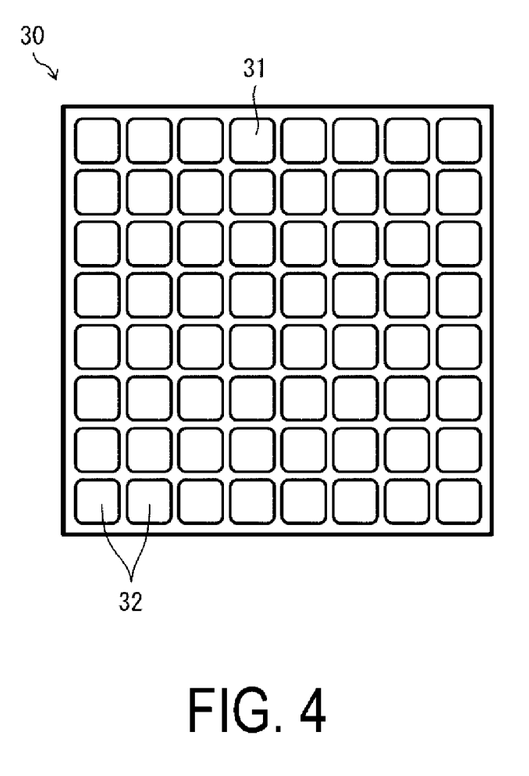
FIG. 4 is a plan view illustrating a schematic configuration of a light receiving unit included in the heating cooking apparatus illustrated in FIG. 1.
Figure 5:
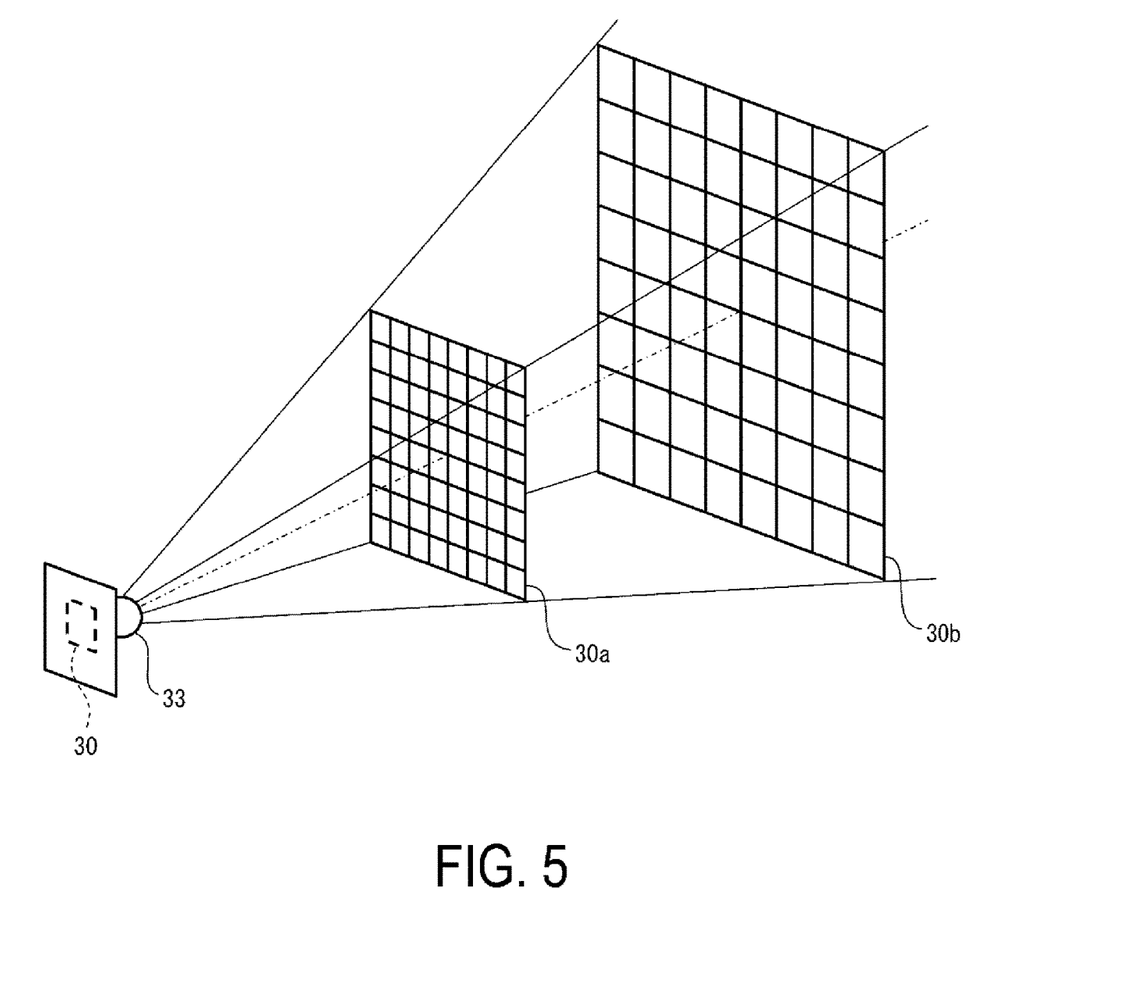
FIG. 5 is a diagram illustrating a visual field image in the light receiving unit illustrated in FIG. 4.

FIG. 4 is a plan view illustrating a schematic configuration of the light receiving unit 30. FIG. 5 is a diagram illustrating a visual field image of the light receiving unit 30 illustrated in FIG. 4. Here, the visual field image indicates an image when the arrangement surface of the light receiving element 32 in the light receiving unit 30 is enlarged. That is, one square represented by the visual field image corresponds to one of the light receiving elements 32 in the light receiving unit 30.

As illustrated in FIG. 4, the light receiving unit 30 is provided with a total of 64 light receiving elements 32, 8 columns in the vertical direction and 8 rows in the horizontal direction, on a light receiving sensor substrate 31. The light receiving element 32 outputs an electrical signal in accordance with the intensity of the received light. In this example, the number of the light receiving elements 32 is 64, but the number is not limited thereto.

On the light receiving surface of the light receiving unit 30, an optical film (not illustrated) that causes each light receiving element 32 to selectively receive light having a wavelength of 600 nm or less is provided. That is, each light receiving element 32 of the light receiving unit 30 receives light having the wavelength of 600 nm or less.

Additionally, as illustrated in FIG. 5, a convex lens 33 is provided on the light receiving surface of the light receiving unit 30. With the convex lens 33, the visual field image of the light receiving surface of the light receiving unit 30 is enlarged as illustrated by reference numerals 30a and 30b. Here, one square of the visual field image indicates a light receiving region received by each light receiving element 32 of the light receiving unit 30. Therefore, in a case where the convex lens 33 is provided, the light receiving region on which each light receiving element 32 receives light can be widened. Note that the convex lens 33 is not an essential component and may not be provided.

The light receiving unit 30 transmits an electrical signal obtained by converting the reflected light from the bread 2 received by each light receiving element 32 to the surface condition determination unit 11. Here, the electrical signal obtained by converting the reflected light received by the light receiving element 32 becomes strong when the intensity of the received light of the received reflected light is strong, and becomes weak when the intensity of the received light of the received reflected light is weak. That is, when the intensity of the received light is strong, the value of the electrical signal becomes large, and when the intensity of the received light is weak, the value of the electrical signal becomes small.

Note that, as described above, the light receiving unit 30 may include the plurality of light receiving elements 32, but may include one light receiving element 32. In this case, the convex lens 33 is disposed in front of the light receiving element 32 to expand the light receiving region, and this allows the reflected light from the foodstuff such as the bread 2 to be received.

Determination of Browned Condition

The surface condition determination unit 11 determines the browned condition of the bread 2 from the electrical signal corresponding to the intensity of the received light of the reflected light having a wavelength of 600 nm or less received by each light receiving element 32 transmitted from the light receiving unit 30. Here, the surface of the bread 2 corresponds to a light receiving region of each light receiving element 32 (one square of the visual field image in FIG. 5). Thus, the surface condition determination unit 11 can determine the browned condition of the surface of the bread 2 corresponding to each light receiving region, that is, how much the surface of the bread 2 is browned, from the electrical signal corresponding to the intensity of received light in the light receiving region of the light receiving unit 30 corresponding to the surface of the bread 2.

Note that the surface condition determination unit 11 preferably determines the browned condition continuously during the cooking of the bread 2. That is, in a case where the surface condition determination unit 11 continuously determines the browned condition on the surface of the bread 2 being cooked, the bread is prevented from being browned insufficiently or from being browned excessively. However, the surface condition determination unit 11 does not need to continuously determine the browned condition during cooking, and may determine the browned condition at predetermined time intervals. Further, the determination by the surface condition determination unit 11 may be started immediately after the start of cooking or after a predetermined time has passed after the start of cooking. The predetermined time after the start of cooking may be set as the time from the start of cooking until the surface condition of the object to be heated first changes. The predetermined time may be set by the user on the operation panel 40, or may be preset for each foodstuff.

Heating Control

The heating control unit 12 receives the determination result from the surface condition determination unit 11 and controls the heating using the heater 50 in accordance with the browned condition of the surface of the bread 2. That is, when the determination result from the surface condition determination unit 11 indicates that the browned condition of the surface of the bread 2 is not in an intended browned condition, the heating control unit 12 causes the heater 50 to continue heating. On the other hand, when the determination result from the surface condition determination section 11 indicates that the browned condition of the surface of the bread 2 is the intended browned condition, the heating control unit 12 stops the heating by the heater 50. Note that even when heating by the heater 50 is stopped, the bread 2 in the heating chamber 1a is heated by the residual heat, so that the browning may proceed. Therefore, the heating by the heater 50 is preferably stopped immediately before the browned condition of the surface of the bread 2 becomes the intended browned condition.

Further, the determination result of the surface condition determination unit 11 may be stored in the storage unit 13 and used when cooking the same foodstuff by heating.

Effects

As described above, according to the toaster 101 according to the disclosure, the light having a wavelength of 600 nm or less, which responds sensitively to the progress of browning of the bread 2, can be selectively monitored, and light in other wavelength regions can be excluded. Accordingly, the electrical signal in accordance with the intensity of the reflected light, which is a more accurate response signal with less noise, can be obtained. As a result, it becomes possible to grasp the condition and change of the surface of the bread 2 that is the target foodstuff to be heated. In particular, for the browning on the surface of the bread 2, which rapidly changes darker, it is important to detect the initial stage of coloring on the surface of the bread 2 as soon as possible, and the toaster 101 according to the present disclosure makes this possible.

Further, the light receiving unit 30 includes a plurality of light receiving elements 32. This allows the inside of the heating chamber 1a of the toaster 101 to be monitored in a more finely divided state. As a result, more information such as an arrangement of the foodstuff such as the bread 2 to be heated and a partial change on the surface of the foodstuff can be obtained.

Further, in a case where the change in the obtained electrical signal is observed, the surface condition determination unit 11 can predict the result of the surface change of the foodstuff being cooked. As a result, the heating control unit 12 can perform more accurate heating control.

Then, the storage unit 13 stores the result of the heating control performed more accurately. On the other hand, when performing the next heating control, the surface condition determination unit 11 and the heating control unit 12 can control the heating based on the user's preference, and can provide a suitably browned bread 2 matching the user's preference by utilizing the results stored in the storage unit 13.

In the embodiment, an example has been described in which the light source 20 in which the wavelength of the emitted light is not particularly limited is used as a light source for determining the browned condition of the bread 2 and the wavelength selection is performed in the light receiving unit 30. In a second embodiment below, an example will be described in which a light source having a wavelength necessary for determining the browned condition of the bread 2 (wavelength of 600 nm or less) is used as the light source 20, and the wavelength selection is not performed in the light receiving unit 30.

Second Embodiment

Another embodiment of the disclosure will be described below. Note that, for convenience of description, components having the same function as those described in the above-described embodiment will be denoted by the same reference signs, and descriptions of those components will be omitted.

The configuration of the toaster 101 is the same as that of the first embodiment of FIG. 1, but differs in the wavelength of the light emitted by the light source 20. In the embodiment, the wavelength of the light emitted by the light source 20 is 600 nm or less.

When the light source 20 emits light having a wavelength of 600 nm or less, the light receiving unit 30 is not required to include the optical filter for wavelength selection.

Note that, in the first and second embodiments, the example has been described in which a common light receiving element capable of receiving light having a wide range of wavelengths including the light in the visible light region is used as the light receiving element 32 of the light receiving unit 30. However, as the light receiving element 32, a light receiving element capable of selectively receiving light having a wavelength of 600 nm or less, or a wavelength in a range from 360 nm to 600 nm may be used. In this case, the light receiving unit 30 is not required to include the optical filter for wavelength selection, and the common light source may be used as the light source 20.

Further, in the first and second embodiments, the example has been described in which the light receiving unit 30 uses an element that outputs an electrical signal according to the intensity of received light, such as the light receiving element 32. However, the disclosure is not limited thereto. For example, the light receiving unit 30 may be a camera, that is, an image capturing element such as a Charge Coupled Device (CCD) sensor or a Complementary Metal Oxide Semiconductor (CMOS) sensor. In a third embodiment, an example in which an image capturing element is used instead of the light receiving element 32 of the light receiving unit 30 will be described.

Third Embodiment

Another embodiment of the disclosure will be described below. Note that, for convenience of description, components having the same function as those described in the above-described embodiment will be denoted by the same reference signs, and descriptions of those components will be omitted.

The configuration of the toaster 101 is the same as that of the first embodiment of FIG. 1, but differs in the device used in the light receiving unit 30. In the embodiment, an example will be described in which the light receiving element 32 constituting the light receiving unit 30 is replaced with a CCD sensor, which is one type of image capturing element.

The configuration of the light receiving unit 30 is the same as the configuration illustrated in FIG. 4, and the light receiving element 32 is replaced with the CCD sensor.

A pixel included in the CCD sensor (hereinafter, referred to as a CCD pixel) converts light into an electrical signal, similar to the light receiving element 32. However, since the resolution of the CCD pixel for the light intensity is inferior to that of the light receiving element 32, a large number of CCD pixels are required to determine the browned condition of the bread 2 using the CCD sensor. That is, in the case of the light receiving element 32, the browned condition of the bread 2 can be determined by the intensity of the received light; however, in the case of the CCD sensor, the browned condition of the bread 2 is determined by combining the area of the CCD pixel that has received light and the intensity of the received light by each pixel.

When the CCD sensor is used, the user can determine the browned condition by himself/herself by displaying an image obtained by capturing an image of the surface of the bread 2 on a monitor (not illustrated) of the operation panel 40 or the like. In addition to this, the application of the CCD sensor in various ways can be developed as follows. For example, the video of the heating cooking process can be recorded for fun. In addition, when the heating cooking apparatus according to the embodiment is used for various foodstuffs such as bread, pizza, meat, and fish, on the basis of the image captured with the CCD sensor before starting heat cooking, image recognition processing is performed on the object to be heated placed in the chamber to identify the size and type of foodstuff. Then, the heating cooking apparatus according to the embodiment can perform the heating cooking automatically using a suitable heating setting prepared in advance or propose the optimum heating program menu for the user by the monitor display.

In the case of the embodiment, similar to the first embodiment, the light source 20 in which the wavelength of the emitted light is not particularly limited may be used, or, similar to the second embodiment, the light source 20 may be used in which the wavelength of the emitted light is limited to 600 nm or less.

Note that in the first to third embodiments, the examples in which the determination device according to the disclosure is applied to the toaster have been described, but the disclosure is not limited thereto. For example, the determination device of the disclosure may be applied to other heating cooking apparatuses such as a convection microwave oven and a microwave oven. Further, the determination device of the disclosure may be applied not only to the heating cooking apparatuses but also to a device that changes the surface of the foodstuff by emitting light.

Supplement

A determination device according to a first aspect of the disclosure includes a light receiving unit (30) configured to receive reflected light from a foodstuff (bread (2)) being cooked and a surface condition determination unit (11) configured to determine a surface condition of the foodstuff (bread (2)) being cooked on the basis of intensity of the reflected light received by the light receiving unit (30).

According to the above configuration, the surface condition of the foodstuff is determined by the intensity of the reflected light from the foodstuff being cooked, so that the surface condition of the foodstuff being cooked can be easily grasped. That is, determining the surface condition of the foodstuff being cooked on the basis of the intensity of the reflected light from the foodstuff is close to determining the surface condition of the foodstuff with the human eye. Thus, the surface condition of the foodstuff being cooked can be determined quickly and accurately compared to a case where the surface condition of the foodstuff is determined using the temperature and humidity in the cooking chamber.

In the determination device according to a second aspect of the disclosure, in the first aspect, the surface condition determination unit (11) may determine the surface condition of the foodstuff (bread (2)) by the reflected light having a wavelength in the range of 600 nm or less in the reflected light from the foodstuff (bread 2) received by the light receiving unit (30).

According to the above configuration, since the surface condition of the foodstuff is determined by the reflected light having a wavelength that responds sensitively to the progress of the browning, a progress condition of the browning of the foodstuff can be determined more appropriately.

In the determination device according to a third aspect of the disclosure, in the second aspect, an optical filter (33) configured to transmit light having a wavelength in a range of 600 nm or less may be provided on a light receiving surface of the light receiving unit (30).

The determination device according to a fourth aspect of the disclosure, in the second aspect, further includes a light source (20) configured to emit light to the foodstuff (bread (2)) being cooked, and the light source (20) may be a light source configured to emit light having a wavelength in a range of 600 nm or less.

According to the above configuration, even when the light receiving unit that selectively receives light having a wavelength in the range of 600 nm or less is not used, or even when the light receiving unit that receives light having a wide range of wavelengths including common visible light is used, progress of browning can be monitored.

In the determination device according to a fifth aspect of the disclosure, in any one of the above first to fourth aspects, the light receiving unit (30) may include a plurality of light receiving elements (32) configured to convert received light into an electrical signal having intensity corresponding to intensity of the received light.

According to the above configuration, the surface condition of the foodstuff being cooked can be determined by the intensity of the electrical signal from the light receiving element.

In the determination device according to a sixth aspect of the disclosure, in any one of the above first to fourth aspects, the light receiving unit (30) may include a plurality of image capturing elements.

According to the above configuration, the surface condition of the foodstuff can be determined from the surface image of the foodstuff being cooked captured by the image capturing elements.

In the determination device according to a seventh aspect of the disclosure, in any one of the above first to sixth aspects, the surface condition determination unit (11) may continuously determine the surface condition of the foodstuff (bread (2)).

According to the above configuration, since the surface condition of the foodstuff being cooked is continuously determined, excess and insufficient cooking, such that the foodstuff is browned insufficiently or is browned excessively, can be prevented.

A heating cooking apparatus according to an eighth aspect of the disclosure includes the determination device according to any one of the above first to seventh aspects and a heating control device (heating control unit (12)) configured to control heating cooking of a foodstuff in accordance with a determination result of the determination device.

According to the above configuration, since the surface condition of the foodstuff being cooked can be appropriately determined, the foodstuff can be cooked by heating in a desired condition.

The heating cooking apparatus according to a ninth aspect of the disclosure, in the eighth aspect, may further include a storage device (storage unit (13)) configured to store a determination result of the determination device, and the heating control device (heating control unit (12)) may control heat cooking of the foodstuff (bread (2)) with reference to the determination result stored in the storage device (storage unit (13)).

According to the above configuration, since the past determination result is utilized, the foodstuff can be cooked by heating according to the preference of the user who has utilized the heating cooking apparatus in the past.

The disclosure is not limited to each of the above-described embodiments. It is possible to make various modifications within the scope of the claims. An embodiment obtained by appropriately combining technical elements each disclosed in different embodiments falls also within the technical scope of the disclosure. Furthermore, technical elements disclosed in the respective embodiments may be combined to provide a new technical feature.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A determination device comprising:
   a light receiving unit configured to receive reflected light from a foodstuff being cooked; and
   a surface condition determination unit configured to determine a surface condition of the foodstuff being cooked on the basis of an intensity ratio of the reflected light received by the light receiving unit,
   wherein the intensity ratio of the reflected light comprises:
      a first intensity value of the reflect light from the foodstuff before a heating process; and
      a second intensity value of the reflected light from the foodstuff after the heating process,
      wherein the intensity ratio is determined by the second intensity value over the first intensity value.

2. The determination device according to claim 1, wherein the surface condition determination unit is further configured to determine the surface condition of the foodstuff by reflected light, having a wavelength of 600 nm or less from the foodstuff, received by the light receiving unit.

3. The determination device according to claim 2, wherein an optical filter configured to transmit light having a wavelength of 600 nm or less is provided on a light receiving surface of the light receiving unit.

4. The determination device according to claim 2, further comprising
   a light source configured to emit light to the foodstuff being cooked,
   wherein the light source is configured to emit light having a wavelength of 600 nm or less.

5. The determination device according to claim 1, wherein the light receiving unit includes a plurality of light receiving elements configured to convert received light into an electrical signal having intensity corresponding to intensity of the received light.

6. The determination device according to claim 1, wherein the light receiving unit includes a plurality of image capturing elements.

7. The determination device according to claim 1,
wherein the surface condition determination unit is further configured to continuously determine the surface condition of the foodstuff.

8. A heating cooking apparatus comprising:
the determination device according to claim 1; and
a heating control device configured to control heat-cooking of the foodstuff in accordance with a determination result of the determination device.

9. The heating cooking apparatus according to claim 8 further comprising:
a storage device configured to store the determination result of the determination device,
wherein the heating control device controls heat-cooking of the foodstuff with reference to the determination result stored in the storage device.

* * * * *